United States Patent [19]
Smith, III

[11] Patent Number: 5,514,082
[45] Date of Patent: May 7, 1996

[54] KNEE BRACE FOR MAINTAINING THE PATELLA AWAY FROM AN IRRITATED AREA OF THE KNEE

[76] Inventor: Kirby Smith, III, 3640 Blakeford Way NE., Marietta, Ga. 30062

[21] Appl. No.: 406,449

[22] Filed: Mar. 20, 1995

Related U.S. Application Data

[62] Division of Ser. No. 207,780, Mar. 8, 1994, Pat. No. 5,433,699.

[51] Int. Cl.⁶ .................................................. A61F 5/00
[52] U.S. Cl. .................................... 602/26; 602/23
[58] Field of Search ................................ 602/5, 23, 26

[56] References Cited

U.S. PATENT DOCUMENTS

| | | | |
|---|---|---|---|
| 1,517,915 | 12/1924 | Masland | 602/26 |
| 3,958,569 | 5/1976 | Vosburgh | 602/26 X |
| 4,854,308 | 8/1989 | Drillio | 602/26 X |
| 4,955,369 | 9/1990 | Bledsoe et al. | 602/26 X |

*Primary Examiner*—Linda C. Dvorak
*Attorney, Agent, or Firm*—Caesar, Rivise, Bernstein, Cohen & Pokotilow, Ltd.

[57] ABSTRACT

Knee braces for various uses, e.g., restricting anterior tibial movement. The braces include a frame, leg mounting straps, and a pressure applicator. The frame is made up of an integral unit including a pair of elongated support rods and a bridging member connecting the rods. In one embodiment the pressure applicator comprises a posterior thigh restraining strap, a portion of the bridging member and a calf cuff pivotally connected to that portion of the bridging member by a single anterior pivot so that the calf cuff can pivot about plural axes with respect to the bridging member. The frame is movably coupled to the upper leg of the person so that the rods can translate forwardly, along the medial and lateral sides of the upper leg, respectively, until the restraining strap resists such forward movement. With the pressure applicator projecting outward from the axes of the rods for fixed anterior positioning relative to the tibia tubercle of the person and with the forward translation of the rods being restrained, resistance to anterior movement of the tibia increases as the person's knee is extended. In another embodiment the brace is arranged to be mounted on the lower leg of the person so that the bridging member applies pressure to the patella and thereby isolate it from the irritated tibia tubercle to reduce the pain associated with Osgood Schlatter's Disease. In another embodiment the brace includes a web of elastic material having a patellar opening for mounting over the patella of the person to aid in patellar tracking.

5 Claims, 8 Drawing Sheets

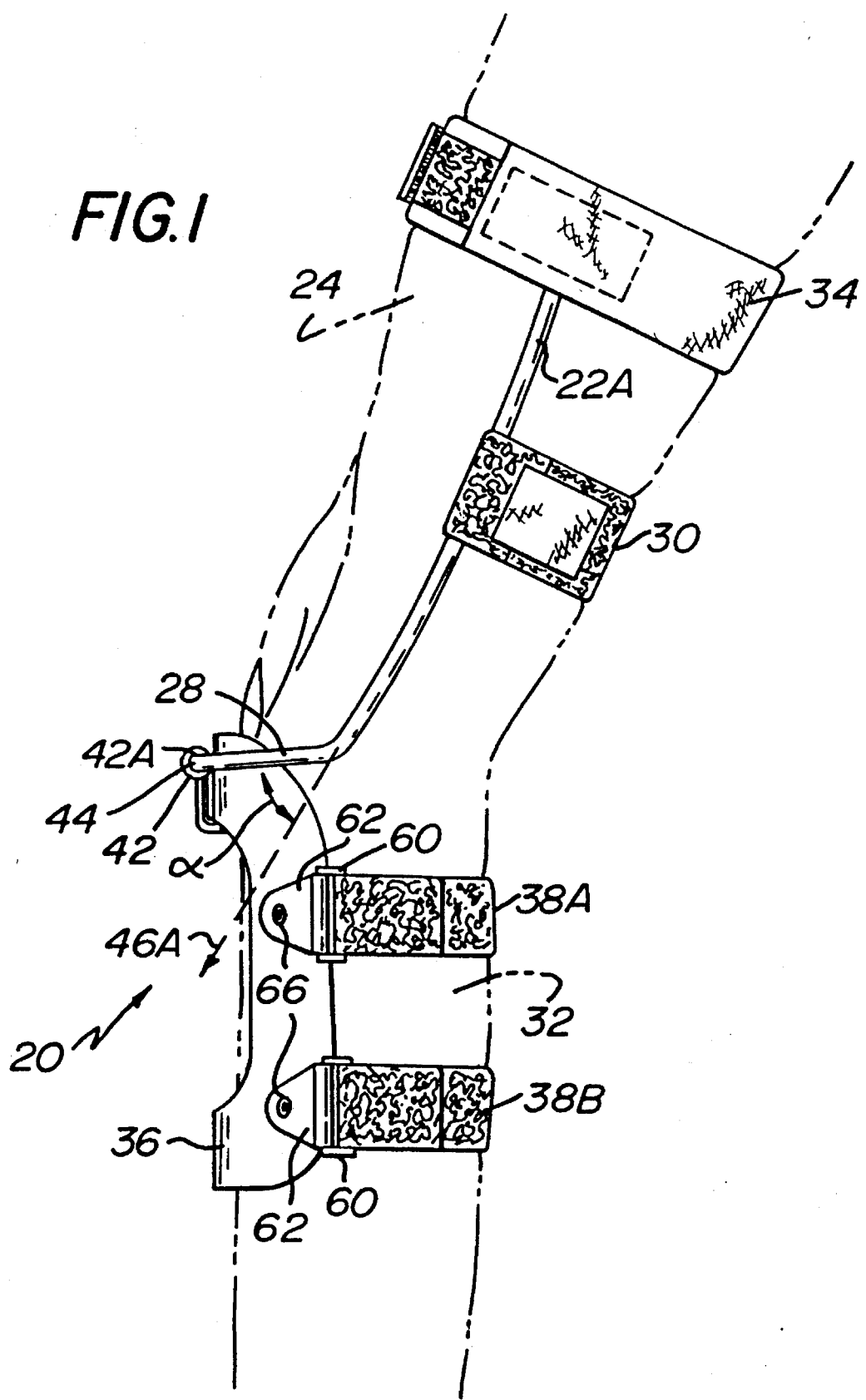

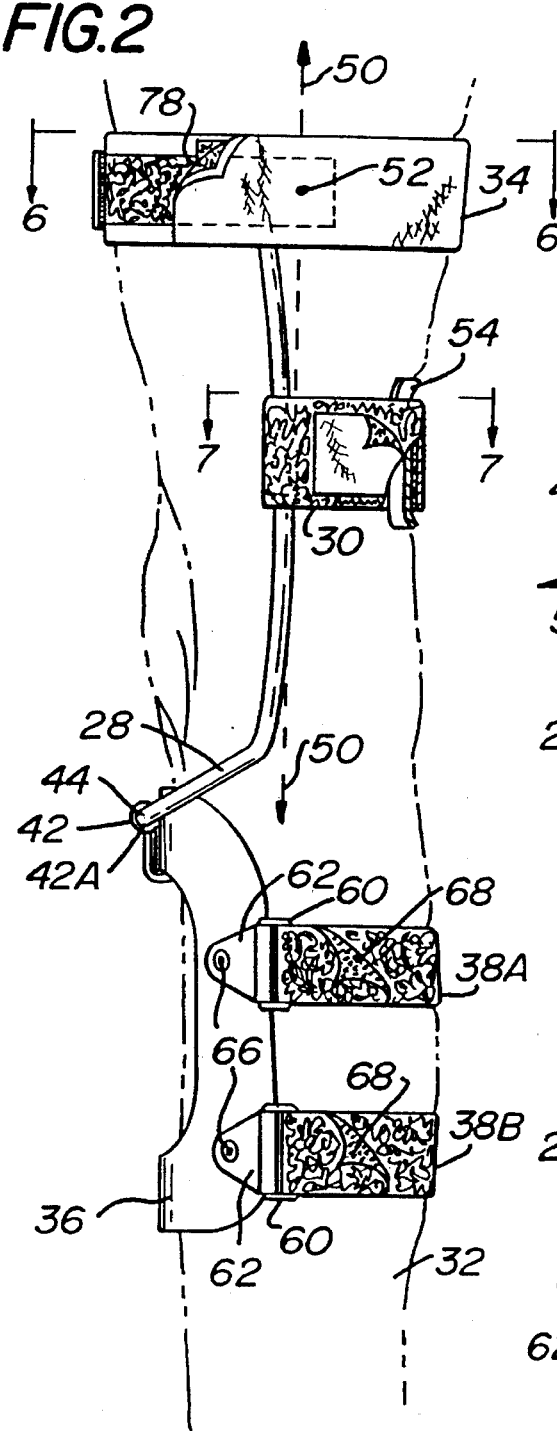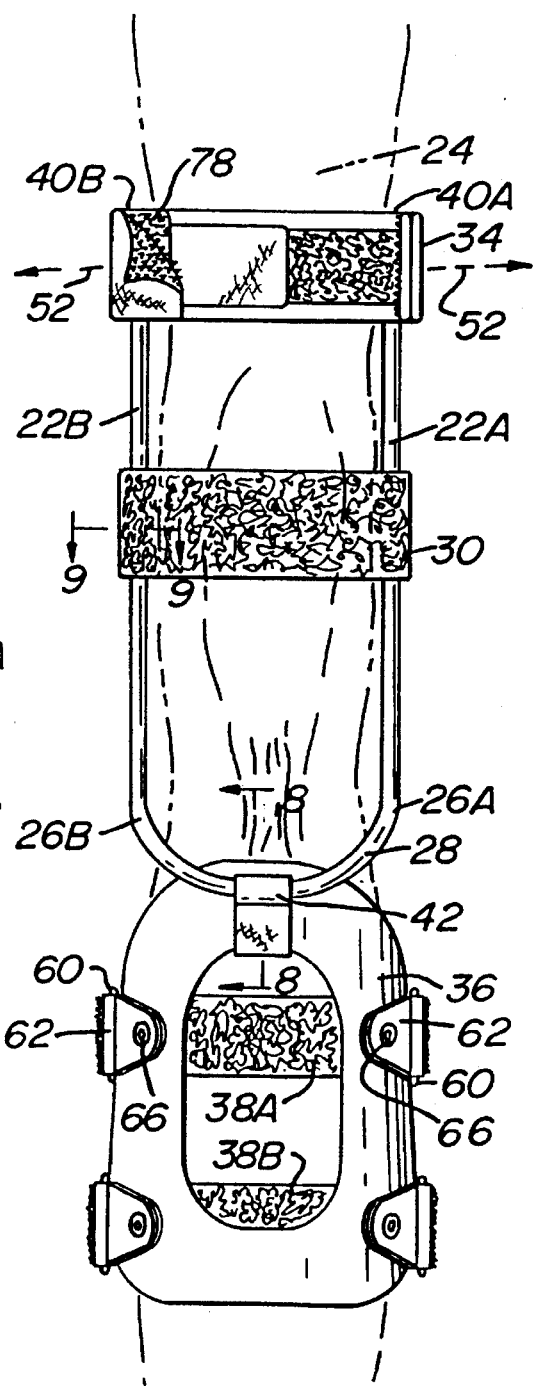

KNEE BRACE FOR MAINTAINING THE PATELLA AWAY FROM AN IRRITATED AREA OF THE KNEE

This application is a divisional of application Ser. No. 08/207,780, filed on Mar. 8, 1994, now U.S. Pat. No. 5,433,699.

SPECIFICATION

This invention relates generally to orthopedic knee braces, and more particularly to knee braces for use by persons having anterior cruciate ligament laxity or insufficiency to protect them from injury due to abnormal anterior tibial movement.

BACKGROUND OF THE INVENTION

Various types of knee braces are shown in the patent literature and are commercially available. The following constitute examples of prior art braces that deal with restricting anterior movement of the tibia found in the following U.S. Pat. Nos. 4,751,920 (Mauldin et al.); 4,781,180 (Solomonow) and 4,955,369 (Bledsoe, et al).

The apparatus shown by Mauldin is a knee brace that has a first attachment portion to attach the brace to the wearer's thigh and a second attachment portion to attach the brace to the wearer's tibia and a hinge connected to the medial side of the first and second attachment portions by way of a thigh bar and tibia bar, respectively. An adjustable gearing mechanism located at the hinge permits the wearer to limit the amount of rotation of the tibia bar with respect to the thigh bar. However, this brace suffers from failing to be able to prevent anterior translation of the tibia by the application of posterior pressure directly at the tibia tubercle location. Instead, like its predecessors, the Mauldin apparatus attempts to limit tibial rotation by limiting medial hinge motion.

The apparatus shown by Solomonow is a knee brace having an upper framework attached to the thigh and a lower framework attached to the lower leg just below the knee. These two frameworks are hinged on the medial and lateral sides of the leg (bilateral hinge). A bell crank is pivotally connected to the lower framework. An adjustable screw coupled to one side of the bell crank engages an offset portion of the upper framework whenever the leg is extended. The other side of the bell crank is coupled to a tibial restraining strap. As the leg is extended, the lower framework and bell crank are rotated counterclockwise until the offset of the upper framework contacts the screw, rotating the bell crank in a clockwise direction and thereby tightening the tibial restraining strap against anterior movement of the tibia.

The apparatus shown by Bledsoe et. al is a knee brace which also utilizes bilateral hinges to connect the thigh support and calf support sections. The bilateral hinges basically comprise adjustable drive plates that alternate the pivoting point of the thigh support and calf support throughout leg flexion and extension. By varying the pivot point at different points throughout leg extension, a counter shearing force is generated to reduce the shearing force created by the quadriceps muscle which cause the undesirable anterior shift of the tibia of the leg.

Examples of prior art knee braces which are commercially available are: DONJOY 4-Point™, GoldPoint™ and Playmaker™ all of which are sold by Smith & Nephew Donjoy Inc. of Carlsbad, Calif. Innovation Sports C.T.I. Standard, Super-Light and Pro-Start, C.T.I.$^2$, MVP, and Sentry all of which are sold by Innovation Sports of Irvine, Calif. Cincinatti ACL which is sold by Brace Technologies Inc. of Cincinatti, Ohio. OS-5™ which is sold by Omni Scientific, Inc. of Martinez, Calif. and the Lennox Hill™ OTS and Spectralite which are sold by 3M Health Care of Long Island City, N.Y. Many of the foregoing braces, while suitable for their intended purposes nevertheless suffer from a common problem, namely, they fail to adequately restrict abnormal anterior tibial movement. All of these conventional braces, basically, comprise a top cuff (or pad), a bottom cuff (or pad), a hinge in the middle (located on the medial side, lateral side or on both of these sides of the leg, i.e., bilateral hinge) and straps to affix the brace to the leg. Although such configurations are satisfactory for dealing with side-of-the-knee injuries, these braces permit the natural motion of the leg which means that they also do not prevent anterior translation of the tibia.

Another type of knee disorder that is common in adolescent males is known as Osgood Schlatter's Disease (OSD). OSD is the partial tearing of a growing tibial tubercle, manifested by subcutaneous swelling over the tibial tubercle and is aggravated by running or by kneeling on, or sustaining direct blows to, the tibia tubercle location. A conventional method of treating OSD is by the use of a device known as a Cho-Pat strap which is sold by Cho-Pat, Inc. of Hainesport, N.J. This strap alleviates the pain associated with OSD by maintaining the patella out of the way of the irritated area. In particular, the strap encompasses the entire circumference about the knee, just under the patella. The disadvantage of this device is that it must be tied tightly about the knee, cutting off blood flow to the calf causing cramping. Moreover, because the strap encompasses the entire circumference of the knee, it tends to bind or encumber the knee location whenever the wearer bends his knee, i.e., it is uncomfortable during sitting or squatting.

Another type of knee disorder is an untracked patella. In a normal knee, as the knee is bent, the patella orients itself into the trochlear groove. When the leg is extended, the patella emerges from that groove. In some cases during this extension, this removal from the trochlear groove makes the patella vulnerable by going out of socket. To guide the patella and ensure that it tracks freely and smoothly, the conventional means used is, in essence, a sleeve with a hole located at the patella which surrounds the knee cap. However, the disadvantage of this design is that as the leg is extended, i.e., when the patella is most vulnerable, the hole puckers, thereby reducing tension applied around the knee cap. Reduction in tension during extension is just the opposite of what is needed: one wants tension to increase around the knee cap as the knee is extended in order to keep the patella aligned.

OBJECTS OF THE INVENTION

Accordingly, it is the general object of this invention to provide a knee brace which overcomes the disadvantages of the prior art.

It is a another object of this invention to provide a knee brace for restricting abnormal anterior tibial movement.

It is a further object of this invention to provide a knee brace for restricting abnormal anterior tibial movement without preventing the wearer from being able to fully extend his/her leg.

It is still yet another object of this invention to provide such a brace that is less expensive than the conventional knee brace.

It is still a further object of this invention to provide such a brace that is lightweight.

It is still a further object of this invention to provide a brace for treating Osgood Schlatter's Disease that does not require a strap be tightly affixed around the lower leg, just under the patella, which reduces blood flow to the calf, causing cramping.

It is still a further object of this invention to provide a brace for treating Osgood Schlatter's Disease that does not bind or put pressure behind the knee area when the leg is flexed.

It is still yet a further object of this invention to provide a brace for aiding in patellar tracking.

It is still yet a further object of this invention to provide a brace for aiding in patellar tracking that increases tension, necessary for proper tracking, to the patella as the leg is extended.

SUMMARY OF THE INVENTION

These and other objects of the instant invention are achieved by providing a knee brace restricting anterior tibial movement of a person comprising translatable frame means, frame mounting means, restraining means, and tibial pressure application means. The frame means comprises a pair of elongated support rods each having an upper end and a lower end, and a bridging member connecting the lower ends of said support rods. Each of the support rods has a longitudinal axis.

The restraining means is connected between the support rods for receipt of a portion of the posterior of the person's upper leg therein. The tibial pressure application means comprises a first portion of the bridging member.

The support rods are coupled, e.g., releasably secured, to the frame mounting means for mounting the support rods on the upper leg of the person wearing the brace so that they extend respectively along the medial and lateral sides of the upper leg, with the tibial pressure application means projecting forwardly outward from the axes of the support rods so that the tibial pressure application means can be brought into a fixed anterior position relative to the tibia tubercle of the person when the leg of the person is extended.

The upper end of each support rod is also movably coupled to the frame mounting means in such a manner, whereupon when the leg of the person is extended the movable coupling of the upper ends of said support rods to the frame mounting means enables the support rods to pivotally translate in a forward direction so that their respective axes are disposed generally parallel to the longitudinal axis of the upper leg. The restraining means serves to oppose the forward pivotal translation so that the tibial pressure application means is held in a fixed anterior position relative to the tibia tubercle of the person to provide resistance to anterior movement of the tibia when the leg is extended.

The upper end of each support rod is also movably coupled to the frame mounting means in such a manner, whereupon when the leg of the person is bent the movable coupling of the upper ends of the support rods to the frame mounting means enables the support rods to pivotally translate in a rearward direction so that their respective axes are disposed at an acute angle with respect to the longitudinal axis of the upper leg of the person, thereby releasing the resistance to the anterior movement of the tibia.

In accordance with one preferred embodiment of the invention the knee brace includes cuff means for securement to the calf of the person. The cuff means comprises an engagement portion for engaging the lower leg of the person contiguous with the tibia tubercle. The engagement portion of the cuff means is preferably coupled to the tibial pressure application means by articulating hinge means.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is a side view of the knee brace for restricting anterior tibial movement attached to the patient's leg (shown in phantom) during partial leg extension;

FIG. 2 is a side view similar to that of FIG. 1 but showing the patient's leg during full leg extension;

FIG. 3 is a front view of the knee brace on the fully extended leg (shown in phantom);

DETAILED DESCRIPTION OF THE PREFERRED EMBODIMENT

Figure 4:
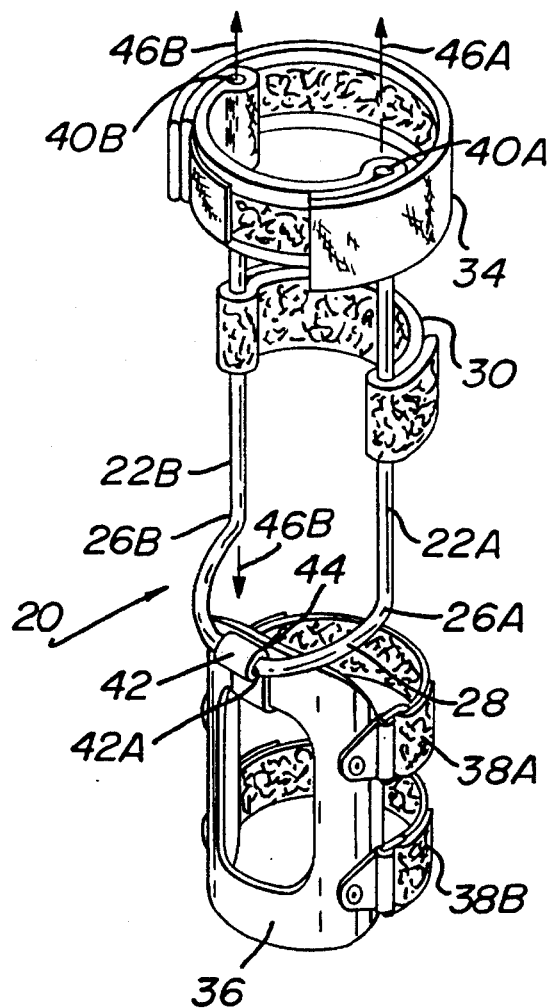
FIG. 4 is a reduced isometric view of the knee brace of FIG. 1.

Referring now in detail to the various figures of the drawing wherein like reference characters refer to like parts, there is shown at 20 in FIG. 1 a knee brace constructed in accordance with this invention attached to the wearer's right leg. (The right leg is chosen for convenience only; this device can be affixed to either the right or left leg). As more clearly shown in FIG. 4, the brace 20 comprises a pair of elongated support rods, 22A and 22B, that are positioned on the medial and lateral sides of the upper leg 24 (FIG. 1), respectively. The two support rods 22A and 22B are coupled to one another at their respective lower ends 26A and 26B by way of a bridging member 28, thereby forming a "U-shaped" frame which can be more easily seen in FIG. 3. The center portion of the bridging member 28 serves to apply pressure to the tibia and hence defines the tibia pressure application means 44 (to be described later).

The support rods 22A and 22B are also coupled to one another at their midsections by way of a restraining strap 30. As will be discussed later, this restraining strap 30 fits snugly around the back portion of the thigh of the wearer's upper leg 24 while coupling the midsections of the support rods 22A and 22B together. The support rods 22A and 22B, bridging member 28 and restraining strap 30 are coupled to the wearer's leg by way of a frame mounting means (to be described hereinafter).

Figure 6:
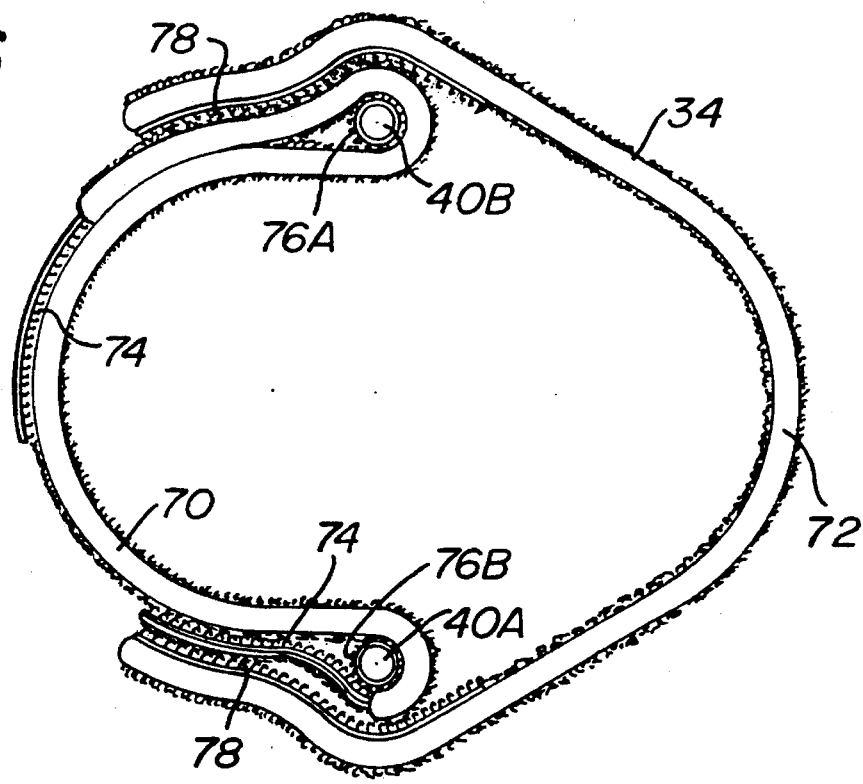
FIG. 6 is an enlarged sectional view taken along line 6—6 of FIG. 2.

The frame mounting means releasably secures the "U-shaped" frame to the upper leg 24 and calf 32 of the wearer and comprises an upper strap 34 that encircles the upper leg 24, a calf cuff 36, and associated calf cuff straps 38A and 38B that affix the brace 20 to the wearer's calf 32. As can be seen in FIGS. 3 and 4, the upper strap 34 couples the upper ends 40A and 40B, respectively, of the support rods 22A and 22B to the upper leg 24. Furthermore, as can be seen in FIG. 6, and as will be discussed in more detail later, this coupling is movable, allowing the support rods 22A and 22B to pivotally translate in a forward or backward direction with respect to the longitudinal axis of the wearer's upper leg about their upper ends 40A and 40B. It should be noted at the outset that the components of this frame mounting means are by way of example and not limitation, i.e., a variety of different attachment configurations could be easily substituted for these straps 34, 38A and 38B and cuff 36. The details of these items will be discussed later.

The calf cuff 36 is mounted on bridging member 28 by way of an articulating hinge 42. As will be discussed later, this hinge 42 maintains the tibial pressure application means 44 at a fixed anterior position relative to the tibia tubercle (not shown) of the wearer, such that increasing pressure is applied to the tibia as the wearer causes his/her leg to be extended, thereby resisting undesirable anterior movement of the tibia. Because it is an articulating hinge, hinge 42 can orient the tibial pressure application means in a position to maintain pressure against the tibia regardless if the leg is turned right or left. Again, it should be noted at the outset that the articulating hinge 42 is by way of example and not limitation, i.e., a variety of different articulating hinges could be easily substituted for the hinge 42.

Figure 5:
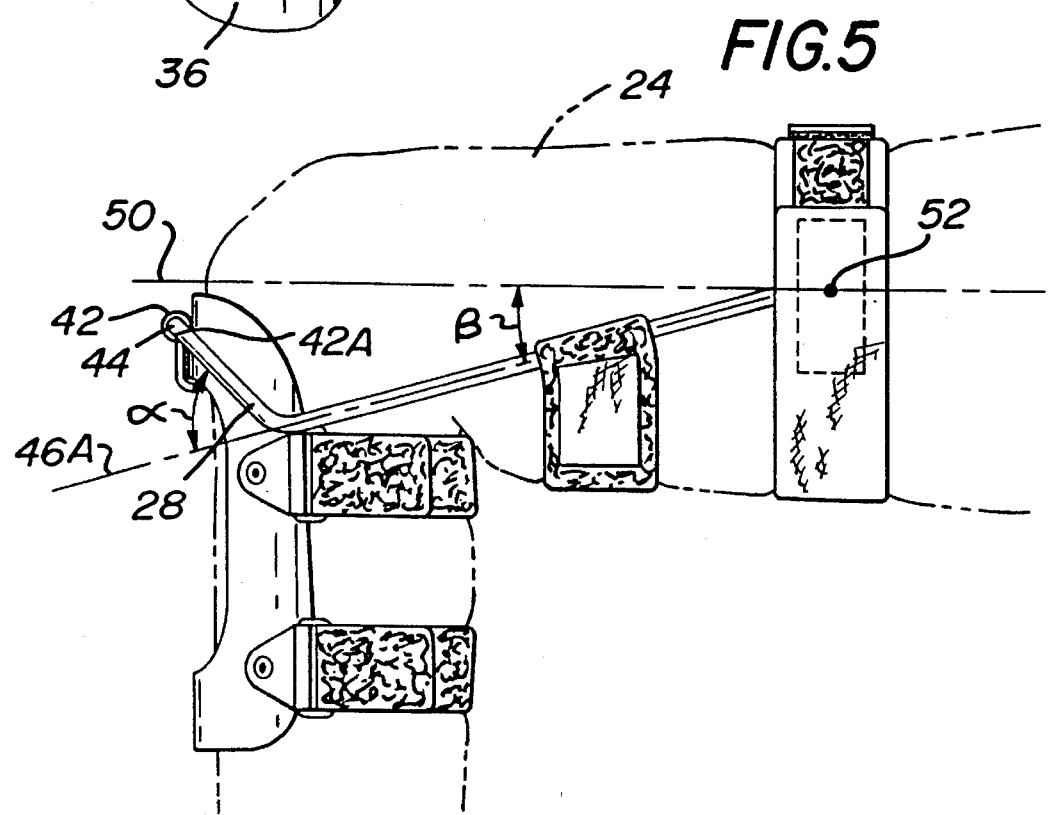
FIG. 5 is a side view of the knee brace like that of FIG. 1 but showing patient's leg when the knee is bent at approximately 90°.

The bridging member 28 is offset from each support rod 22A by a predetermined angle α with respect to each of the longitudinal axes 46A and 46B (FIG. 4) of the support rod 22A and 22B, respectively. The offset α is selected to be in the range of between 30° and 60° with respect to the longitudinal axes 46A and 46B, as shown in FIG. 5. This offset assures that the support rods 22A and 22B remain situated along the medial and lateral sides of the leg, respectively, throughout the entire range of leg movement, i.e., from a bent knee (FIG. 5, hereinafter known as the "90° position") to full extension (FIG. 2, hereinafter known as the "0° position"). Without the offset α, i.e., if the frame were co-planar, extending the leg would drive the frame out of position. Instead the offset bridging member 28 allows the leg to be pivoted into the space bounded by the offset bridging member 28 until the tibial pressure application means 44 makes contact with the tibial tubercle. Furthermore, since the bridging member 28 is of an arcuate shape (FIG. 4) it can abut the area surrounding the knee when the leg is fully extended, while minimizing the amount of projection away from the knee that the bridging member 28 exhibits when the leg is bent (FIG. 5). Therefore, the combination of the offset α and the arcuate shape of the bridging member 28 maintain the bridging member as close to the knee as possible throughout full knee flexion and extension.

Operation of the knee brace 20 can be explained as follows. Starting in FIG. 5, at the 90° position (where the knee is bent), there is no pressure being asserted against the tibia by the bridging member 28 at the hinge 42 location. Note that the longitudinal axis 46A of support rod 22A forms an acute angle β with respect to the longitudinal axis 50 of the upper leg 24 of the wearer when the knee is bent. The angle β is between 0° and approximately 30°. As the leg is extended, the upper ends 40A and 40B of the support rods 22A and 22B pivot about an axis 52 normal to the medial side of the upper leg 24 (FIGS. 2 and 3), whereby the lower ends of support rods 22A and 22B translate in a forward direction so that the support rod axes 46A and 46B assume a position generally parallel to the upper thigh longitudinal axis 50 as shown in FIG. 2. The restraining strap 30 tends to resist this forward translation. This resistance causes the tibial pressure application means 44 (to be described later) to be held in a fixed anterior position relative to the tibia tubercle (not shown) of the wearer, thereby creating a resistive force in the posterior direction against anterior movement of the tibia when it engages the tibial pressure application means 44. This resistive force is first sensed by the wearer when the leg has been extended down to approximately the 30° position and increases as the leg reaches the fully extended position due to the opposition of the restraining strap 30 to the support rods' 22A and 22B forward translation. When the leg reaches the 0° position (i.e., fully extended as shown in FIG. 2), the restraining strap 30 maintains the support rods 22A and 22B such that their respective longitudinal axes, 46A and 46B are generally parallel to the upper thigh longitudinal axis 50. In this position, the resistive force against the tibia, provided by the tibial pressure application means 44, is at its maximum, thereby preventing any further forward translation of the tibia.

As shown in FIGS. 1 and 2, the restraining force exerted by the restraining strap 30 tends to "bow" the support rods 22A and 22B somewhat, thereby preventing any further forward translation of the support rods, 22A and 22B, and thereby anchoring the bridging member 28 with respect to the leg. This latter action prevents any forward movement of the tibia. These views (shown in FIGS. 1 and 2) are exaggerated in that the amount of "bow" of the supporting rods due to the restraining strap 30 may actually be very subtle.

Because the restraining strap 30 resists the forward translation of the support rods 22A and 22B, the strap 30 may tend to "dig" or "bite" into the wearer's posterior portion of the thigh. Therefore, a shield 54 (FIG. 2) is provided for insertion between that portion of the wearer's thigh and the restraining strap 30 to eliminate any discomfort caused by the tightening strap 30.

The operation of the brace from full extension to flexion is as follows when the wearer flexes his or her leg: starting from the 0° position and then flexing his or her leg towards the 90° position, as the calf 32 reaches the 30° position the resistive force diminishes as the support rods 22A and 22B translate in a rearward direction, pivoting about their upper ends 40A and 40B towards the posterior of the thigh. Therefore, the restraining strap 30 relaxes and there is no longer any resistive force being applied to the tibia. The support rods 22A and 22B come to rest in a position where their respective longitudinal axes 46A and 46B form the acute angle β, thereby maintaining the bridging member 28 and articulating hinge 42 close to the knee location, while not obstructing any further flexion of the leg.

The following discussion concerns the detail of the indicated components of the knee brace 20.

The frame, composed of the rods 22A and 22B and the bridging member 28, is preferably formed as an integral unit of any suitable strong material, e.g., carbon graphite, preferably fiberglass with carbon fiber braid. Even aircraft aluminum could be used.

As can be seen in FIG. 4 and appreciated by those skilled in the art, the upper end of the cuff 36 provides a surface upon which a portion of the articulating hinge 42 is fixedly secured. The articulating hinge 42 will be described in detail later with reference to FIG. 8. Suffice it for now to state that it basically comprises a strap of any suitable flexible material, e.g., woven nylon which is folded over itself to form a passageway 42A through which the central portion of the bridging member 28 extends. The strap forming the hinge extends through a horizontal slot in the upper end of the cuff 36 and is held in place by cooperating VELCRO® fasteners.

Figure 15:
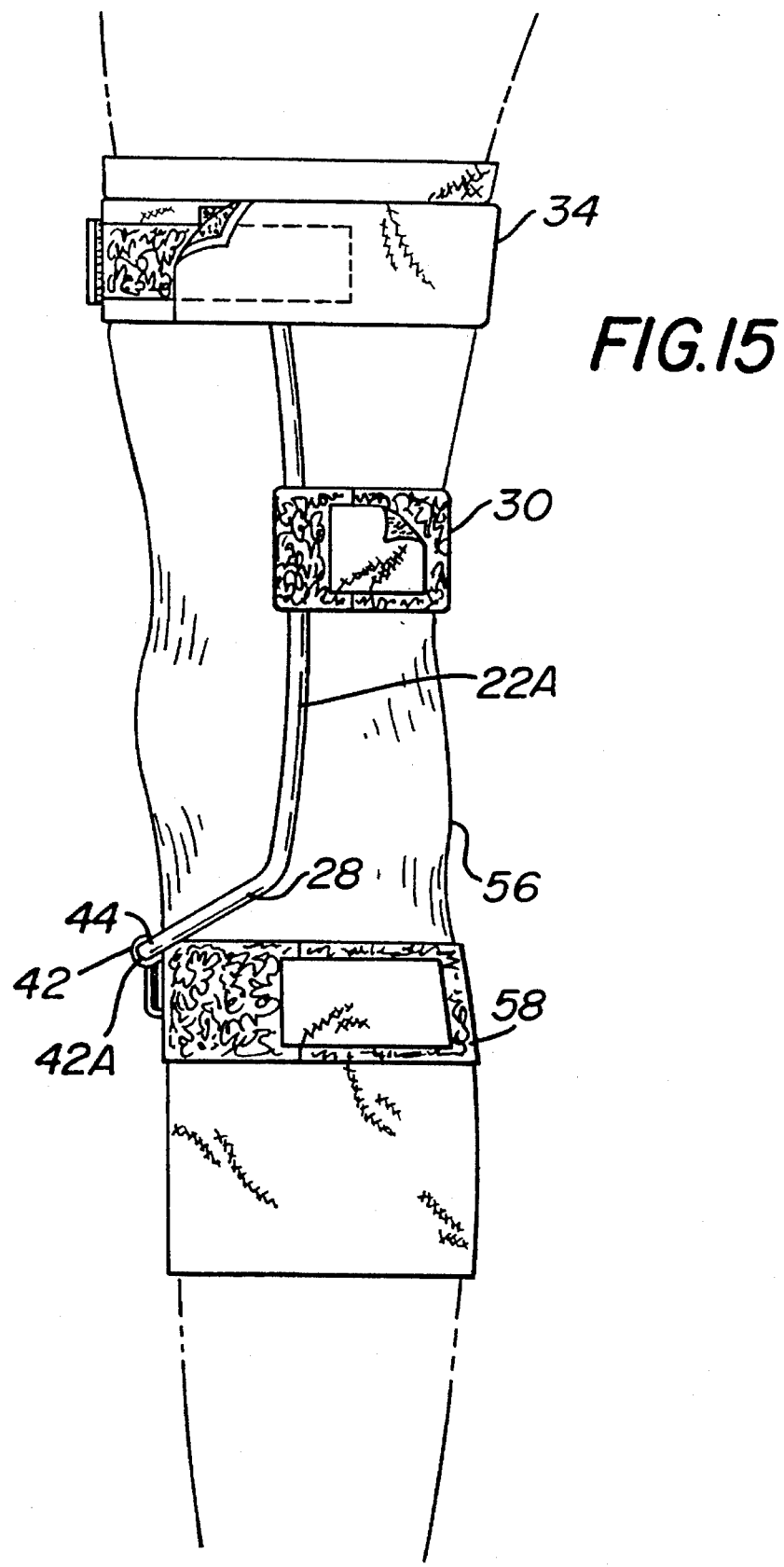
FIG. 15 is a side view of yet another embodiment of the knee brace for restricting anterior tibial movement using a neoprene sleeve attached to the patient's leg during full leg extension.

Any means, e.g., a neoprene sleeve 56 (FIG. 15), can be used in lieu of the cuff 36 to mount the articulating hinge 42 on the bridging member 28. If such a sleeve is used, an additional strap 58 is necessary to secure the support rods 22A and 22B to the front of the leg. If a rigid cuff 36 is used, the cuff is preferably made of polyethylene (or any copolymer). Certainly, because the cuff 36, as shown in FIGS. 1–5, comprises a rigid surface, the effect of having the articulating hinge 42 mounted thereon results in the upper portion of the cuff 36 aiding the bridging member 28 in distributing the force against anterior translation of the tibia.

As stated previously, the upper cuff strap 38A and lower cuff strap 38B provide the releasable securement of the cuff 36 to the calf 32. Each strap 38A and 38B is slipped through and then looped around rings 60. The rings 60 are trapped in brackets 62 to form hinged rings. The brackets 62 are coupled to the cuff 36 by way of rivets 66. The ends of straps 38A and 38B each include a VELCRO® hook patch 68 (FIG. 2) that releasably engages the plush outer surface of the straps 38A and 38B. The other ends of the straps 38A and 38B are secured to the cuff 36 via brackets 62 including hinged rings 60. The brackets 62 are riveted to the cuff 36 by rivets 66. The straps 38A and 38B extend through the associated hinged rings 60 and the VELCRO® hook patch 68 on the strap 38A is brought into engagement with the plush surface of the strap 38A, thereby permitting the strap 38A to be tightened or loosened for comfort. The strap 38B is mounted and adjusted in a similar manner.

FIG. 6 depicts a top view of the upper strap 34 which comprises an anterior thigh strap 70 and a posterior thigh strap 72. The anterior thigh strap 70 is looped around support rods 22A and 22B and folded back upon itself, with the inner side of the free ends of strap 70 being in the form of a VELCRO® hook patch 74 that engages the plush outer side of the strap 70. Each upper end 40A and 40B of support rods 22A and 22B, respectively, includes a hook patch 76A and 76B, respectively, of VELCRO® secured about its periphery with the hooks projecting out to releasably engage the plush inner surface of the strap. This looping of the thigh strap 70 to releasably secure the upper ends of the rods creates the movable coupling between the upper ends 40A and 40B of the support rods 22A and 22B to the upper thigh 24 of the wearer while permitting the support rods 22A and 22B to pivotally translate about axis 52. The VELCRO® hook patches 76A and 76B are affixed (e.g., glued) about the circumference of the upper ends 40A and 40B. The ends of the posterior thigh strap 72 also have VELCRO® hook patches 78 that engage the plush outer surface of anterior thigh strap 70. The VELCRO® hook patches 78 provide the means to tighten or loosen the upper strap 34 for correct fit around the upper thigh 24.

Figure 7:
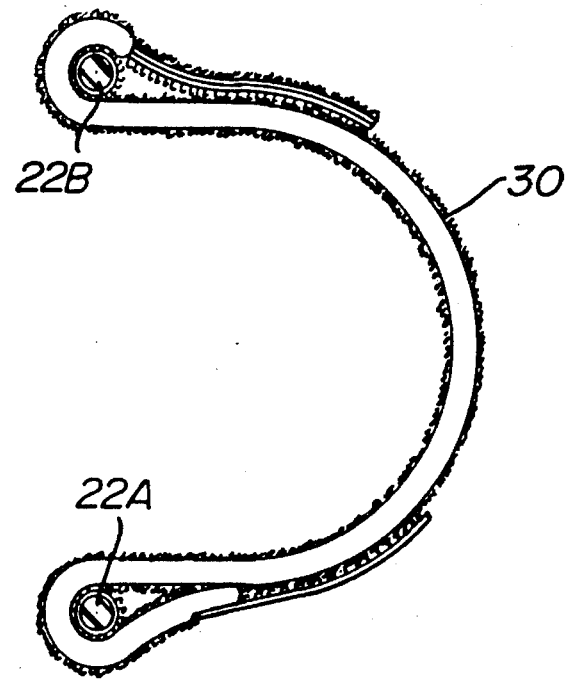
FIG. 7 is an enlarged sectional view taken along line 7—7 of FIG. 2.

FIG. 7 depicts a top view of the restraining strap 30. This strap 30 is attached to the support rods 22A and 22B in the identical manner as described above with regard to the anterior thigh strap 70.

Figure 9:
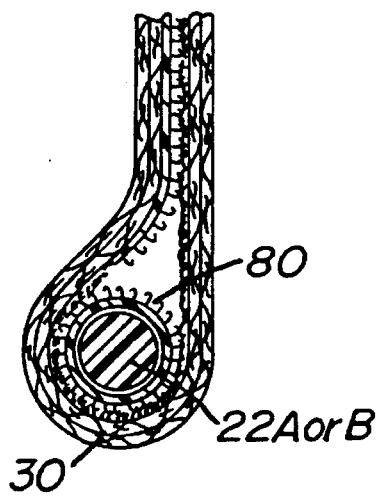
FIG. 9 is an enlarged sectional view taken along line 9—9 of FIG. 3.

FIG. 9 depicts the means by which the restraining strap 30 is looped around one of the support rods. On this regard the support rod 22A (or 22B) has its own VELCRO® hook patch 80 that is affixed (e.g., glued) to engage a plush portion of the restraining strap 30. This engagement assures that the restraining strap 30 maintains its coupling to the support rod 22A and 22B midsections.

Figure 8:
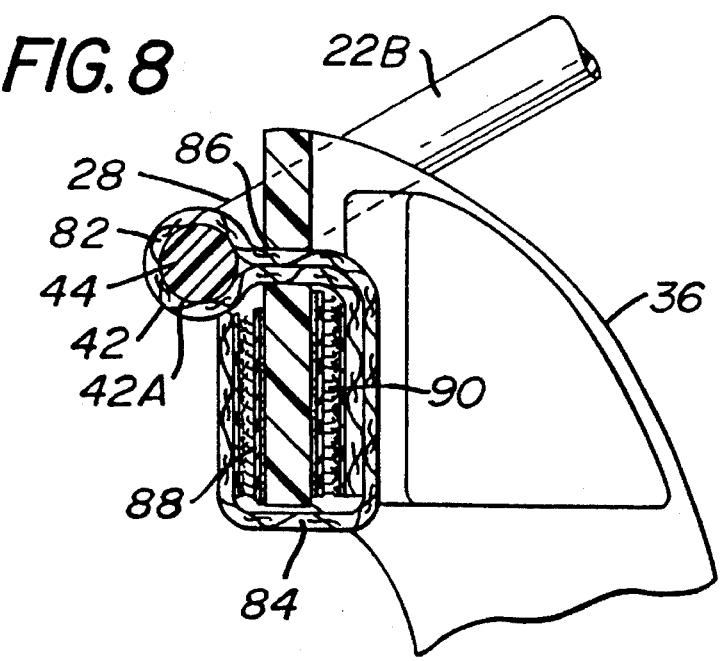
FIG. 8 is an enlarged sectional view taken along line 8—8 of FIG. 3.

FIG. 8 depicts a cross-sectional view of the articulating hinge 42 of FIG. 1. The hinge 42 is formed of a pliable sleeve 82 that is looped to form passageway 42A which receives and traps the central portion of the bridging member 28 therein. The sleeve 82 is formed by a looping of a woven material, e.g., nylon, strip 84 that is affixed through the upper part of cuff 36 by an aperture or slot 86. The sleeve 82 gives the bridging member 28 the ability to articulate in many directions. The material strip 84 loops around the upper portion of the cuff 36 and is then fastened to the cuff's 36 outer surface by a VELCRO® hook patch 88 adhesively secured to the outer surface of the upper end of the cuff 36. An inner VELCRO® plush patch 90 is located on an end of the strap 84 to maintain a tight fit of the material strip 84 to the cuff 36.

Figure 10:
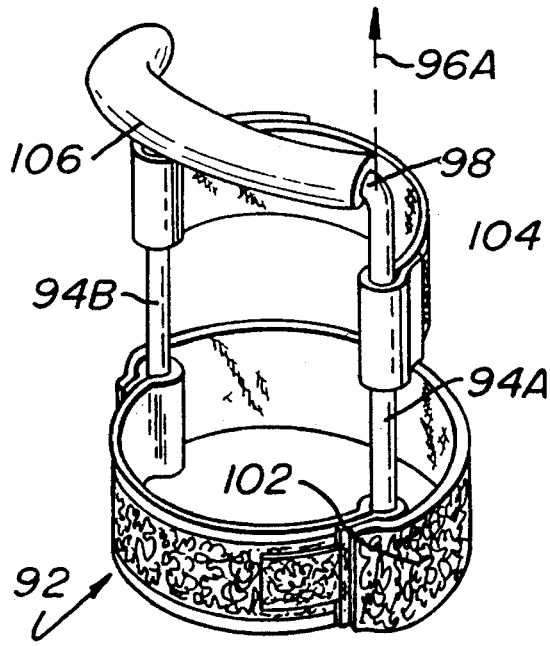
FIG. 10 is an isometric view of an alternative embodiment of the brace for use with patients having Osgood Schlatter's Disease.
Figure 11:
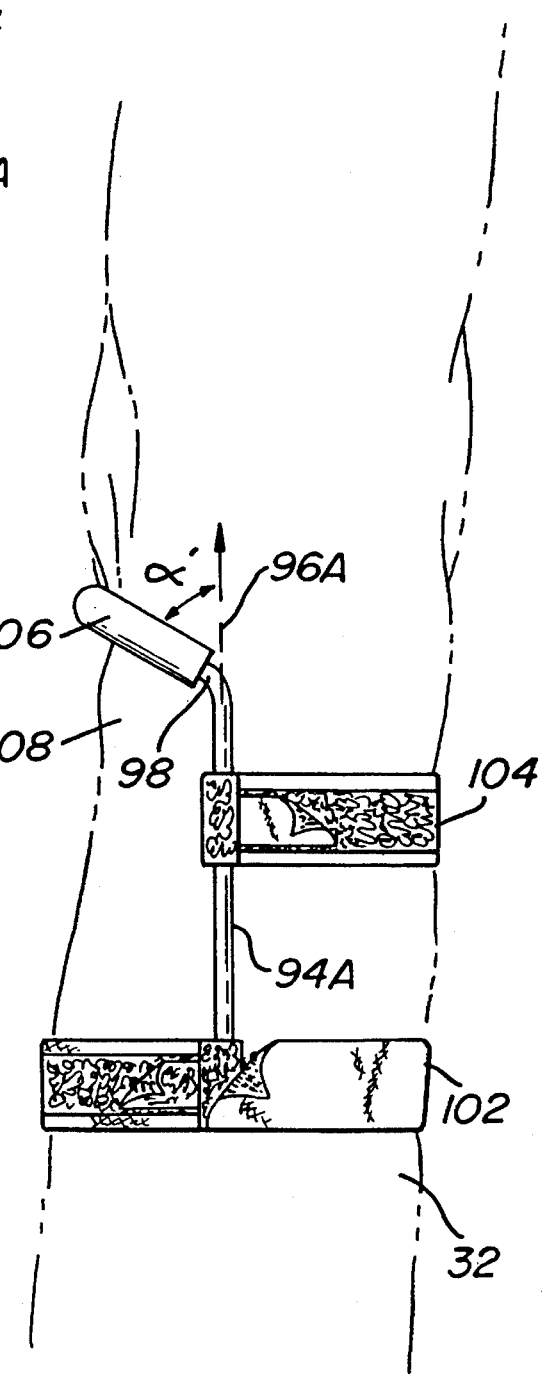
FIG. 11 is a side view of the brace of FIG. 10 shown attached to the patient's leg (shown in phantom)

A similar configuration of this brace can be used in the treatment of Osgood Schlatter's Disease. In FIG. 10, there is shown a brace 92 comprising a frame means, a frame mounting means and a pressure application means. The frame means is basically identical to that of the brace 20 of FIG. 1 and comprises a pair of elongated support rods 94A and 94B, having longitudinal axes 96A and 96B, respectively. The rods are connected to each other by a bridging member 98. As with the bridging member 28, the bridging member 98 is also arcuate in shape and forms an offset α' (FIG. 11) with respect to each support rod longitudinal axis 96A and 96B for purposes similar to the ones discussed above concerning offset α. The frame mounting means comprises a lower strap 102 for affixing the brace 92 to the right calf (as stated earlier, the right calf is chosen for convenience only; the brace 92 could be affixed to either the left or right calf) and a stabilizing strap 104. These straps 102 and 104 are coupled to the support rods 94A and 94B in the same manner as the upper strap 34 and restraining strap 30, respectively, are coupled to support rods 22A and 22B, as discussed above. The pressure application means comprises a portion of the bridging member 98 that rests just under the patella (in particular, the bridging member 98 is oriented at the patella notch, i.e., the distal portion of the patella tendon) when the brace 92 is mounted to the calf 32 and the leg is in an extended position (FIG. 11). A bridging member cushion 106 (e.g., foam cushion) is disposed on the bridging member 98 for the wearer's comfort.

Operation of the brace 92 occurs during extension of the leg as follows. With the brace 92 mounted to the calf 32, the bridging member 98 is located horizontally across the infrapatellar region, between the inferior pole of the patella and the tibial tubercle. As the leg is extended, the bridging member 98 increases pressure on that region to maintain the patella away from the irritated area 108 (e.g., an enlarged tibial tuberosity). As the leg is extended, the patella presses downward against the bridging member 98 which increases its resistance to this downward movement due to the fixed position of the support rods 94A and 94B.

The advantage of this brace 92 over the conventional treatment, the Cho-Pat strap, is that pressure is applied to the patella without reducing blood flow to the leg and thereby avoids cramping of the calf. In addition, when the wearer of the brace 92 is seated or in a squatting position where the knee is bent, there is no encumbrance under the knee to cause discomfort.

Figure 12:
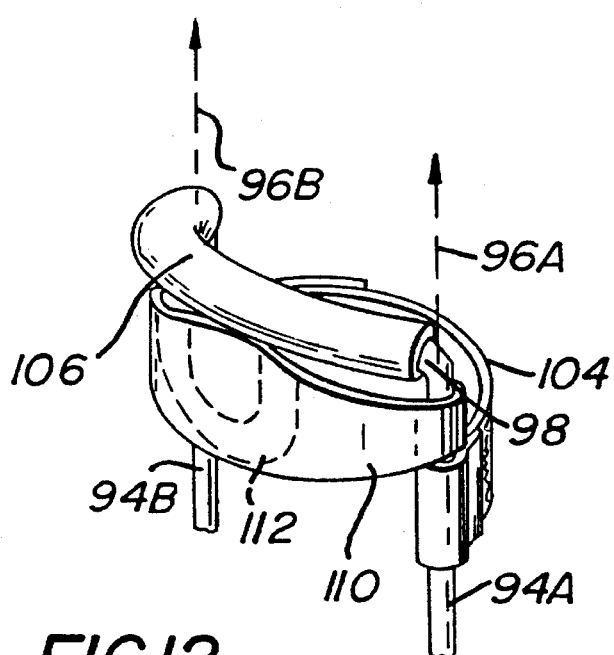
FIG. 12 is a partial isometric view of the brace of FIG. 10 showing an optional protective cover for the tibia tubercle mounted thereon.

An optional protective cover 110 can be coupled to the brace 92, as shown in FIG. 12, to protect the tibial tubercle in addition to treating the pain associated with OSD. The protective cover has a pad 112 on its inner side to create a cushion between the cover 110 and the tibial tubercle location.

Figure 13:
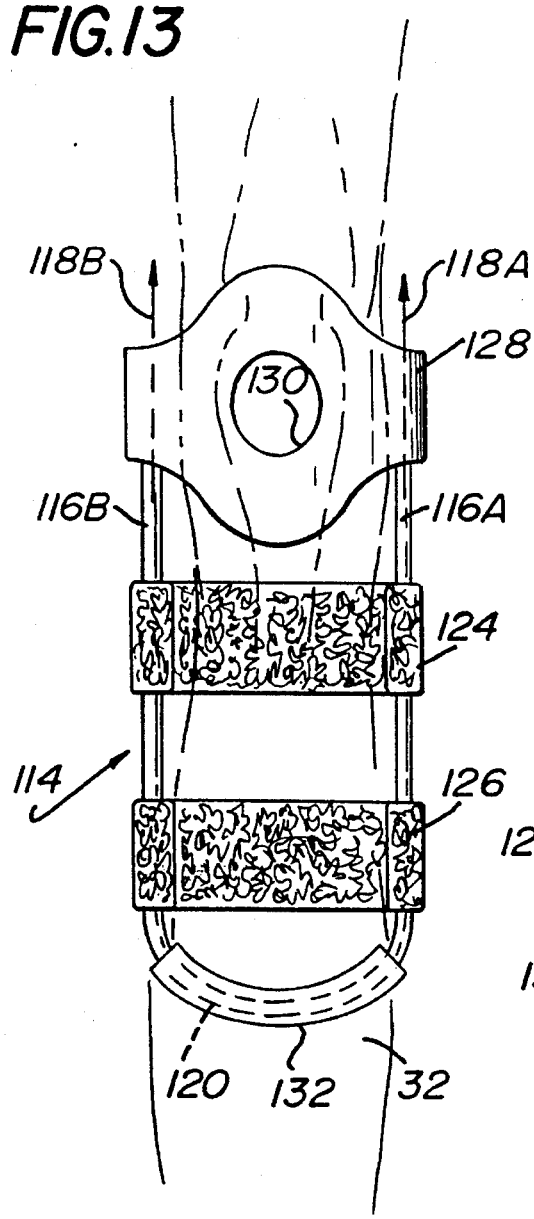
FIG. 13 is a front view similar to FIG. 3 but showing yet another alternative embodiment of a knee brace, this brace being for patellar tracking and is shown during full extension of the leg (shown in phantom)
Figure 14:
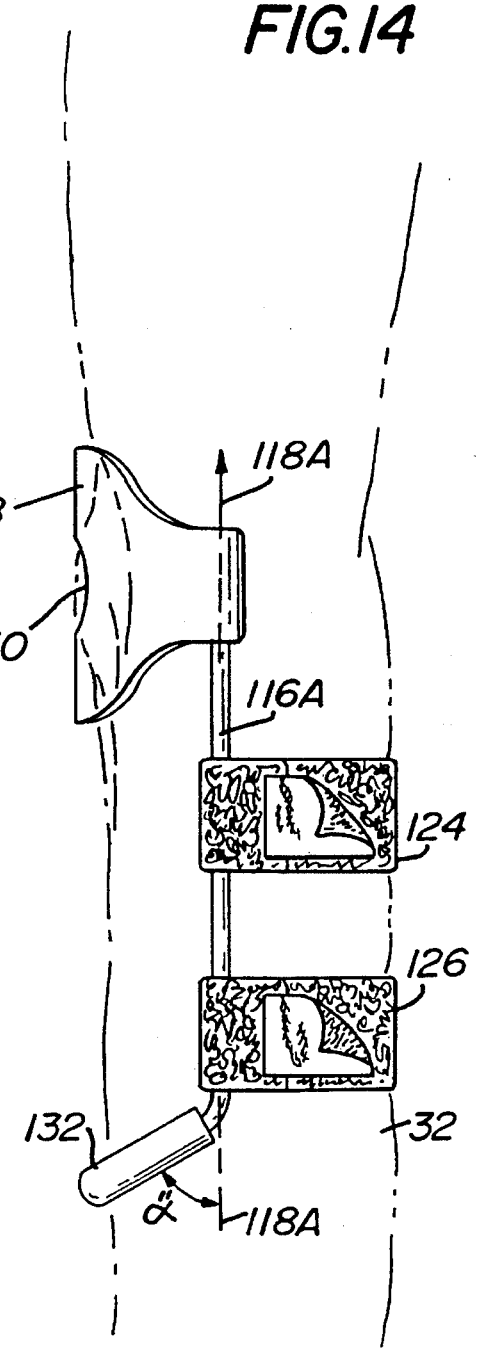
FIG. 14 is a side view similar to FIG. 13 of the knee brace for patellar tracking.

Another similar brace configuration that is used in aiding patellar tracking is shown in FIGS. 13 and 14. This brace 114 comprises a frame means, frame mounting means and a pressure application means. The frame means comprises a pair of elongated rods 116A and 116B, having longitudinal axes 118A and 118B, respectively, and are connected to one another by a bridging member 120. As with the bridging member 28, the bridging member 120 is also arcuate in shape and forms an offset α" (FIG. 14) with respect to each support rod longitudinal axis 118A and 118B for purposes similar to the ones discussed above concerning the offset α. Although in brace 114 the bridging member 120 is disposed over the anterior portion of the calf 32 rather than just under the knee as in the brace 92, the arcuate shape of the bridging member 120 and the offset α" serve to maintain the support rods 116A and 116B along the medial and lateral sides of the calf 32 throughout leg flexion and extension while minimizing the amount of projection of the frame means away from the surface Of the calf 32.

The frame mounting means comprises a middle strap 124 and a lower strap 126. These straps affix and stabilize the elongated rods 116A and 116B along the medial and lateral sides of the right leg calf 32 (the right leg was chosen for convenience only; the brace 114 could be affixed to the left or the right legs). The upper ends of the elongated rods are coupled to the pressure application means, which in this instance comprises a member 128, having a hole 130 that is fitted over the wearer's patella. As the knee is extended from a bent position, the member 128 increases pressure about the patella to maintain the alignment of the patella as it emerges from the trochee groove (not shown). The rods 116A and 116B maintain the member's 128 position on the patella, thereby avoiding the "puckering" that normally occurs in other patellar tracking devices. The member 128 may comprise any variety of materials (e.g., elastic, inelastic or any combination thereof), depending on the amount and direction of pressure to be applied to the patella.

The straps 124 and 126 are attached to the support rods 116A and 116B in a similar manner as the restraining strap 30 is attached to the support rods 22A and 22B. The member 128 is attached to the support rods 116A and 116B in a similar manner as the anterior thigh strap 70 discussed above. A bridging member cushion 132 (e.g., foam cushion) is also disposed around the bridging member 118 for the wearer's comfort.

Without further elaboration, the foregoing will so fully illustrate my invention that others may, by applying current or future knowledge, readily adopt the same for use under various conditions of service.

I claim:

1. A brace for securement on the lower leg of a person to maintain the person's patella away from an adjacent irritated area associated with Osgood Schlatter's Disease while enabling the knee to bend when the brace is in place on the lower leg, said brace comprising frame means, frame mounting means, and pressure application means, said frame means comprising a pair of elongated support rod sections and a bridging section, each of said support rod sections having a longitudinal axis, a lower free end, and a upper end, said bridging section being disposed directly between said upper end of each of said support rod sections to form the top of said brace, said pressure application means comprising a first portion of said bridging section, said support rod sections being coupled to said frame mounting means for securely mounting said frame on the lower leg of the person with said support rod sections extending respectively along the medial and lateral sides of the lower leg of the person and with said pressure application means projecting outward from the axes of said support rods for fixed anterior positioning relative to the tibia tubercle of said person, whereupon said pressure application means maintains the patella away from the irritated area throughout leg extension by applying pressure to the infrapatellar region between the inferior pole of the patella and the tibial tubercle, thereby reducing the pain associated with Osgood Schlatter's Disease.

2. The brace of claim 1 wherein said axes of said support rod sections are disposed parallel to each other, and wherein said bridging section comprises an arcuately shaped member lying in a plane disposed at an acute angle to the axes of said support rod sections.

3. The brace of claim 2 wherein said angle is within the range of approximately 30 to 60 degrees from the axes of said support rod sections.

4. The brace of claim 1 wherein said frame mounting means comprises a lower strap arranged for releasably encircling a portion of the calf of the person, said lower strap being secured to said lower free ends of said support rods.

5. The brace of claim 4 wherein said frame mounting means additionally comprises a stabilizing strap secured to said support rod sections between said lower strap and said upper ends of said support rod sections, said stabilizing strap being arranged for engaging the calf of the person.

* * * * *